(12) United States Patent
Sealey et al.

(10) Patent No.: US 8,771,476 B2
(45) Date of Patent: Jul. 8, 2014

(54) METHODS FOR INHIBITING POLYMERIZATION OF VINYL AROMATIC COMPOUNDS DURING EXTRACTIVE DISTILLATION

(75) Inventors: Amy Sealey, Bozeman, MT (US); George A. Ball, Hampstead, NC (US); B. Bryant Slimp, Jr., Houston, TX (US)

(73) Assignee: GTC Technology LP, Houston, TX (US)

( * ) Notice: Subject to any disclaimer, the term of this patent is extended or adjusted under 35 U.S.C. 154(b) by 324 days.

(21) Appl. No.: 12/705,937

(22) Filed: Feb. 15, 2010

(65) Prior Publication Data

US 2011/0015462 A1    Jan. 20, 2011

Related U.S. Application Data

(60) Provisional application No. 61/226,628, filed on Jul. 17, 2009.

(51) Int. Cl.
*C07C 7/20* (2006.01)
*C07C 7/08* (2006.01)

(52) U.S. Cl.
USPC .......... 203/9; 203/8; 203/50; 203/57; 203/68; 585/833; 585/864

(58) Field of Classification Search
USPC ................. 203/8, 9, 57, 50, 68; 585/833, 864
See application file for complete search history.

(56) References Cited

U.S. PATENT DOCUMENTS

| | | | |
|---|---|---|---|
| 3,684,665 A * | 8/1972 | Abe et al. | 203/9 |
| 3,763,015 A * | 10/1973 | Morimoto et al. | 203/9 |
| 4,033,829 A * | 7/1977 | Higgins et al. | 203/9 |
| 4,182,658 A | 1/1980 | Watson | |
| 4,514,261 A * | 4/1985 | Crum | 203/9 |
| 4,596,655 A * | 6/1986 | van Eijl | 208/348 |
| 5,446,220 A * | 8/1995 | Arhancet | 585/5 |
| 5,849,982 A | 12/1998 | Lee et al. | |
| 5,877,385 A | 3/1999 | Lee et al. | |
| 5,910,232 A * | 6/1999 | Hyde et al. | 203/9 |
| 6,348,136 B1 * | 2/2002 | Ledoux et al. | 203/9 |
| 6,395,943 B1 * | 5/2002 | Kurek et al. | 585/5 |

FOREIGN PATENT DOCUMENTS

GB    2289282 A1 *    11/1995    ............ C07C 7/05

OTHER PUBLICATIONS

Young, Lee W., "International Search Report" for PCT/US10/35889 as mailed Jul. 12, 2010, 2 pages.

* cited by examiner

*Primary Examiner* — In Suk Bullock
*Assistant Examiner* — Bradley Etherton
(74) *Attorney, Agent, or Firm* — Winstead PC

(57) ABSTRACT

High temperatures and oxygen exposure during extractive distillation can result in polymerization of vinyl aromatic compounds. In various embodiments, the present disclosure relates to methods for inhibiting polymerization of vinyl aromatic compounds during extractive distillation. In various embodiments, the methods include a) providing a mixture containing at least one vinyl aromatic compound, b) adding at least one dinitrophenol inhibitor to the mixture, and c) after step b), performing an extractive distillation on the mixture to isolate the at least one vinyl aromatic compound. Purified styrene can be isolated by the methods described herein. In some embodiments, the dinitrophenol inhibitor is 2-sec-butyl-4,6-dinitrophenol (DNBP).

9 Claims, No Drawings

METHODS FOR INHIBITING POLYMERIZATION OF VINYL AROMATIC COMPOUNDS DURING EXTRACTIVE DISTILLATION

CROSS-REFERENCE TO RELATED APPLICATIONS

This application claims priority to U.S. provisional patent application 61/226,628, filed Jul. 17, 2009, which is incorporated by reference herein in its entirety.

STATEMENT REGARDING FEDERALLY SPONSORED RESEARCH

Not applicable.

BACKGROUND

Styrene and related vinyl aromatic compounds are the building blocks for numerous types of industrial products such as, for example, polymers and resins. Styrene can be produced as a commodity chemical through recovery from a hydrocarbon stream (e.g., pyrolysis gasoline) or by dehydrogenation of ethylbenzene. Isolation of a vinyl aromatic compound (e.g., styrene) from a pyrolysis gasoline stream is typically performed by extractive distillation, which typically necessitates exposure of the vinyl aromatic compound to elevated temperatures and/or oxygen. Both of these conditions can initiate unwanted thermal- or free radical-induced polymerization or oligomerization. Polymerization can lead to production losses and eventually result in system blockages of the apparatus being used for separating the vinyl aromatic compound from the hydrocarbon stream.

To lessen polymerization of vinyl aromatic compounds during their isolation from a hydrocarbon stream, extractive distillation is conventionally performed at reduced pressures to minimize oxygen exposure and lower processing temperatures to minimize thermal exposure. Even under the best of circumstances, however, the vinyl aromatic compounds will still come into contact with small quantities of oxygen and be exposed to temperatures ranging from about 80° C. to about 160° C. for time periods ranging from seconds to hours. Thermal-induced polymerization of styrene can occur when the styrene monomer is exposed to temperatures of about 100° C. or higher for only a few minutes. In addition to the aforesaid oxygenation and thermal conditions, the vinyl aromatic compounds may also be exposed to a variety of contaminants in the hydrocarbon source such as, for example, sulfur-containing compounds and colored impurities, that may further promote unwanted polymerization.

Methods are known in the art for minimizing the polymerization of vinyl aromatic compounds, particularly styrene, through adding a small amount of an inhibitor compound to the vinyl aromatic compound in either purified or crude form. For example, dinitrophenolic compounds (e.g., 2,6-dinitro-p-cresol) have been used to inhibit polymerization of vinyl aromatic compounds during vacuum distillation. A combination of a hindered phenol (e.g., a dinitrophenolic compound), optionally a hydroxylamine, and a phenylenediamine have also been used to inhibit vinyl aromatic compound polymerization under oxygen-free conditions or under normal atmospheric conditions. Likewise, a combination of dinitrophenolic compound and a nitroxyl free radical compound of have been used to inhibit vinyl aromatic compound polymerization. A combination of a 2-nitrophenolic compound in combination with a sulfonic acid compound has also been used to inhibit vinyl aromatic compound polymerization.

Although the aforesaid inhibitor systems are generally effective for production and purification of styrene via conventional dehydrogenation of ethylbenzene, Applicants believe that they are unsuitable for extractive distillation of styrene and other vinyl aromatic compounds from a hydrocarbon source such as, for example, pyrolysis gasoline. In view of the foregoing, new methods for inhibiting the polymerization of vinyl aromatic compounds during their isolation from a hydrocarbon stream would generally be beneficial in the art. Recent advances in separations technology make it possible to recover styrene from pyrolysis gasoline derived from the steam cracking of naphtha, gas oils and liquid natural gas. These new separations technologies include conditions of thermal exposure and oxygen exposure that are generally challenging parameters for maintaining stability of styrene and other vinyl aromatic compounds in an unpolymerized state. Embodiments set forth herein are effective in overcoming those challenges.

SUMMARY OF THE INVENTION

In various embodiments, the present disclosure describes methods for inhibiting polymerization of vinyl aromatic compounds during extractive distillation. The methods include steps of a) providing a mixture having at least one vinyl aromatic compound, b) adding at least one dinitrophenol inhibitor to the mixture, and c) after step b) occurs, performing an extractive distillation on the mixture to isolate the at least one vinyl aromatic compound. In some embodiments, a single vinyl aromatic compound is isolated. In some embodiments, the single vinyl aromatic compound is styrene.

The foregoing has outlined rather broadly the features of the present disclosure in order that the detailed description that follows may be better understood. Additional features and advantages of the disclosure will be described hereinafter, which form the subject of the claims.

DETAILED DESCRIPTION OF ILLUSTRATIVE EMBODIMENTS

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

As used herein, the term "aromatic" refers to aromaticity, a chemical property in which a conjugated ring of unsaturated bonds, lone pairs, or empty orbitals exhibit a stabilization stronger than would be expected by the stabilization of conjugation alone. It can also be considered a manifestation of cyclic delocalization and of resonance stabilization. This is usually considered to be because electrons are free to cycle around circular arrangements of atoms, which are alternately single- and double-bonded to one another.

As used herein, the term "aliphatic" refers to compounds having carbon atoms that are capable of being joined together in straight chains, branched chains, or rings (in which case they are called alicyclic). They can be joined by single bonds (alkanes), double bonds (alkenes), or triple bonds (alkanes).

As used herein, the term "polymer" will collectively refer to polymers of vinyl aromatic compounds including dimers, trimers, higher oligomers and polymers.

Other than in the operating examples, or where otherwise indicated, all numbers expressing quantities of components used herein are to be understood to be modified in all instances by the term "about".

Embodiments of the present disclosure are generally directed toward methods for inhibiting thermal- and free radical-induced polymerization of vinyl aromatic compounds during extractive distillation processes. In such extractive distillation processes, vinyl aromatic compounds may be exposed to low levels of oxygen and high temperatures (about 80° C. to about 160° C.) for varying lengths of time. These conditions are conducive toward inducing polymerization of the vinyl aromatic compounds. As demonstrated herein, high levels of a dinitrophenol inhibitor can minimize or substantially prevent polymerization of vinyl aromatic compounds during extractive distillation processes under conditions in which polymer formation occurs within minutes in the absence of an inhibitor. In some embodiments, the dinitrophenol compound is 2-sec-butyl-4,6-dinitrophenol (DNBP), which may be used alone to inhibit polymerization.

In various embodiments, the present disclosure describes methods for inhibiting polymerization of vinyl aromatic compounds during extractive distillation. The methods include steps of a) providing a mixture having at least one vinyl aromatic compound, b) adding at least one dinitrophenol inhibitor to the mixture, and c) after step b) occurs, performing an extractive distillation on the mixture to isolate the at least one vinyl aromatic compound. In some embodiments, the at least one aromatic compound includes styrene. In certain embodiments, a single vinyl aromatic compound is isolated from the extractive distillation. In some embodiments, the single vinyl aromatic compound is styrene.

In various embodiments, the mixture also includes contaminants from which the vinyl aromatic compounds are to be separated. Such contaminants include, for example, aliphatic compounds, aromatic compounds, other vinyl aromatic compounds, sulfur-containing compounds, colored impurities and combinations thereof.

In the discussion that follows, styrene is presented as an illustrative vinyl aromatic compound that can be isolated according to the methods described in the present disclosure. However, one of ordinary skill in the art will recognize that other vinyl aromatic compounds may be isolated through routine experimental modifications of the embodiments described herein, such modifications residing within the spirit and scope of the present disclosure.

In other various embodiments, styrene can be isolated from pyrolysis gasoline using methods described in U.S. Pat. Nos. 5,849,982 and 5,877,385, each of which are incorporated by reference herein in their entirety. Among the teachings of these patents are producing a pyrolysis gasoline heart cut that has been deoctanized and deheptanized to contain about 25% to about 35% styrene. After selective hydrogenation to remove phenylacetylene, extractive distillation is performed to separate styrene from the remaining components of the mixture. The styrene is recovered in a solvent, which is then fed to a solvent recovery column to remove solvent and recover isolated styrene. Recovered solvent is then fed back to the extractive distillation column. During this styrene isolation process, temperatures can reach at least about 100° C. for extended time periods, especially in reboiler systems and extractive distillation column bottoms. Polymer can form and accumulate, leading to system breakdown, under these conditions in the absence of an inhibitor. In various embodiments, the extractive distillation is performed at a temperature of at least about 100° C. In other various embodiments, the extractive distillation is performed at a temperature between about 80° C. and about 160° C.

Although dinitrophenol and related nitrophenol compounds are known in the art, Applicants believe that the present disclosure is the first to demonstrate that high concentrations of these moieties can be used to inhibit polymerization upon exposure to conditions commonly encountered during extractive distillation. In various embodiments, polymerization of vinyl aromatic compounds can be minimized or substantially prevented by adding a dinitrophenol or related nitrophenol inhibitor to a hydrocarbon stream before isolation of the vinyl aromatic compound from the stream. In various embodiments, the dinitrophenol compound is 2-sec-buyl-4,6-dinitrophenol (DNBP). In various embodiments, the hydrocarbon stream is a pyrolysis gasoline stream.

In various embodiments, the polymerization that is inhibited is a thermal-induced polymerization. In other various embodiments, the polymerization that is inhibited is a free radical-induced polymerization.

In various embodiments, a concentration of DNBP or other dinitrophenol inhibitor in the hydrocarbon stream determines the effectiveness of inhibiting polymerization of the vinyl aromatic compound. For example, in the embodiments presented herein, adding DNBP at high concentrations may substantially prevent polymerization of the vinyl aromatic compound. The concentrations of DNBP and other dinitrophenol inhibitors described in the embodiments presented herein are considerably higher than are commonly encountered in other applications in which polymerization of a vinyl aromatic compound is inhibited. In some embodiments of the methods described herein, a concentration of DNBP is at least about 10,000 wt. ppm with respect to the at least one vinyl aromatic compound of interest. In other various embodiments, a concentration of DNBP is between about 10,000 wt. ppm and about 20,000 wt. ppm. In still other various embodiments, a concentration of DNBP is between about 10,000 wt. ppm and about 15,000 wt. ppm. In yet additional embodiments, a concentration of DNBP is about 14,000 wt. ppm.

EXPERIMENTAL EXAMPLE

The following example is provided to more fully illustrate some of the embodiments of disclosed hereinabove. It should be appreciated by those of skill in the art that the techniques disclosed in the example which follows represents techniques that constitute exemplary modes for practice of the disclosure. Those of ordinary skill in the art should, in light of the present disclosure, appreciate that many changes can be made in the specific embodiments that are disclosed and still obtain a like or similar result without departing from the spirit and scope of the disclosure.

In the example that follows, polystyrene analysis was conducted using a modification of ASTM D2121 by precipitating polymer from a styrene/extractive agent mixture using methanol, followed by filtration and drying of the precipitated polymer. The detection limit was 200 wt. ppm polymer.

Example 1

A dinitrophenol inhibited mimetic feed representing a styrene extractive distillation column bottom was prepared where 95% extractive agent was mixed with 5% styrene with and without varying doses of DNBP as shown in Table 1. Table 1 shows data collected from heating a 35 g quantity of the aforesaid mixtures at a temperature 120 to 160° C. for 0 to 180 minutes. Heating was conducted in a pressure-resistant sealed tube. Samples for Time=0 minutes were removed from heat as soon as the sample temperature reached the desired set point temperature. Relative amounts of polystyrene formed during heating is indicated by shading of the cells in the chart.

TABLE 1

Effectiveness of DNBP-Inhibited Extractive Distillation

| Reagent | Temperature (° C.) | Inhibitor wt. ppm with respect to styrene | Inhibitor wt. ppm with respect to total mixture | Time (min) | | | | | |
|---|---|---|---|---|---|---|---|---|---|
| | | | | 0 | 15 | 30 | 60 | 120 | 180 |
| Uninhibited styrene | 160 | N/A | N/A | *** | N/A | N/A | N/A | **** | **** |
| Uninhibited styrene | 150 | N/A | N/A | *** | N/A | N/A | N/A | **** | **** |
| Uninhibited styrene | 140 | N/A | N/A | — | ** | *** | *** | **** | **** |
| Uninhibited styrene | 120 | N/A | N/A | — | — | — | ** | *** | N/A |
| DNBP | 160 | 14,000 | 700 | — | — | — | — | — | — |
| DNBP | 140 | 14,000 | 700 | — | — | — | — | — | — |
| " | " | 4000 | 200 | — | — | — | * | ** | N/A |
| " | " | 2000 | 100 | — | * | ** | *** | *** | N/A |
| " | " | 1000 | 50 | — | * | *** | *** | *** | N/A |
| DNBP | 120 | 14,000 | 700 | — | — | — | — | — | — |
| " | " | 4000 | 200 | — | — | — | — | — | N/A |
| " | " | 2000 | 100 | — | — | — | * | ** | N/A |
| " | " | 1000 | 50 | — | — | — | ** | ** | N/A |

| Polymer concentration (wt ppm) ranges | — | * | ** | *** | **** | MeOH method LOD 200 ppm |
|---|---|---|---|---|---|---|
| | <200 | 200-250 | 250-1000 | 1000-5000 | >5000 | |

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. A method for inhibiting polymerization of vinyl aromatic compounds during extractive distillation, said method comprising the steps of:
   a) providing a mixture;
      wherein the mixture comprises at least one vinyl aromatic compound;
   b) adding an inhibitor consisting of unmodified 2-sec-butyl-4,6-dinitrophenol to the mixture wherein a concentration of the inhibitor is at least about 1,000 wt ppm with respect to the at least one vinyl aromatic compound; and
   c) after step b) occurs, performing an extractive distillation on the mixture to isolate the at least one vinyl aromatic compound; and
      wherein less than 200 wt ppm of polymer is formed from the at least one vinyl aromatic compound.

2. The method of claim 1, the extractive distillation is performed at a temperature of at least about 100° C.

3. The method of claim 1, wherein the extractive distillation is performed at a temperature between about 80° C. and about 160° C.

4. The method of claim 1, wherein a single vinyl aromatic compound is isolated from the extractive distillation.

5. The method of claim 4, wherein the single vinyl aromatic compound is styrene.

6. The method of claim 1, wherein a concentration of the dinitrophenol inhibitor is at least about 10,000 wt ppm with respect to the at least one vinyl aromatic compound.

7. The method of claim 1, wherein the at least one vinyl aromatic compound comprises styrene.

8. The method of claim 1, wherein the polymerization is thermal-induced.

9. The method of claim 1, wherein the polymerization is free radical-induced.

* * * * *